United States Patent
Weldon

(10) Patent No.: US 6,623,440 B1
(45) Date of Patent: Sep. 23, 2003

(54) TOPICAL ANESTHETIC APPLICATOR AND METHOD OF USE

(76) Inventor: Leonard Weldon, 165 S. Lincoln St., Keene, NH (US) 03431

( * ) Notice: Subject to any disclaimer, the term of this patent is extended or adjusted under 35 U.S.C. 154(b) by 0 days.

(21) Appl. No.: 09/717,183

(22) Filed: Nov. 21, 2000

Related U.S. Application Data

(60) Provisional application No. 60/166,879, filed on Nov. 22, 1999.

(51) Int. Cl.⁷ .................. A61M 35/00; A61B 10/00; A47L 13/12
(52) U.S. Cl. ............... 604/1; 600/562; 600/572; 600/569; 15/106; 15/111; 15/159.1; 15/160
(58) Field of Search ................ 604/1–3; 222/187; 600/562, 572, 569; 451/523, 524; 15/106, 111, 159.1, 160

(56) References Cited

U.S. PATENT DOCUMENTS

| | | | |
|---|---|---|---|
| 2,127,094 A | * | 8/1938 | Strauss |
| 3,018,778 A | * | 1/1962 | Brilliant |
| 4,767,398 A | * | 8/1988 | Blasius, Jr. |
| 5,214,820 A | * | 6/1993 | Shumway et al. |
| 5,214,821 A | * | 6/1993 | Burrow et al. |
| 5,715,559 A | * | 2/1998 | Mitri |
| 5,762,494 A | * | 6/1998 | Archambault |
| 5,829,976 A | | 11/1998 | Green ................ 433/89 |
| 5,878,459 A | * | 3/1999 | McParland |
| 6,119,296 A | * | 9/2000 | Noe et al. |
| 6,258,044 B1 | * | 7/2001 | Lonky et al. |
| 6,297,044 B1 | * | 10/2001 | Eisen et al. |

* cited by examiner

*Primary Examiner*—Dennis Ruhl
(74) *Attorney, Agent, or Firm*—Lynne M. Blank

(57) ABSTRACT

The present invention relates to a novel applicator for topical anesthetics and a method using said novel applicator which provides for pain-free injections in mucosa by the application of a topical anesthetic followed by an injection limited to penetrate the mucosa only to the extent of penetration of the topical anesthetic. The method is accomplished by applying a topical anesthetic to the desired mucosal area by means of a novel applicator swab, comprising a handle on which is attached an absorbent material and an abrasive portion. The swab is dipped in topical anesthetic and placed at the desired oral location, where the abrasive portion is used to mildly abrade the oral mucosa. The application of the topical is then followed with an injection which penetrates the tissues only to the extent of penetration of the topical anesthetic.

7 Claims, 1 Drawing Sheet

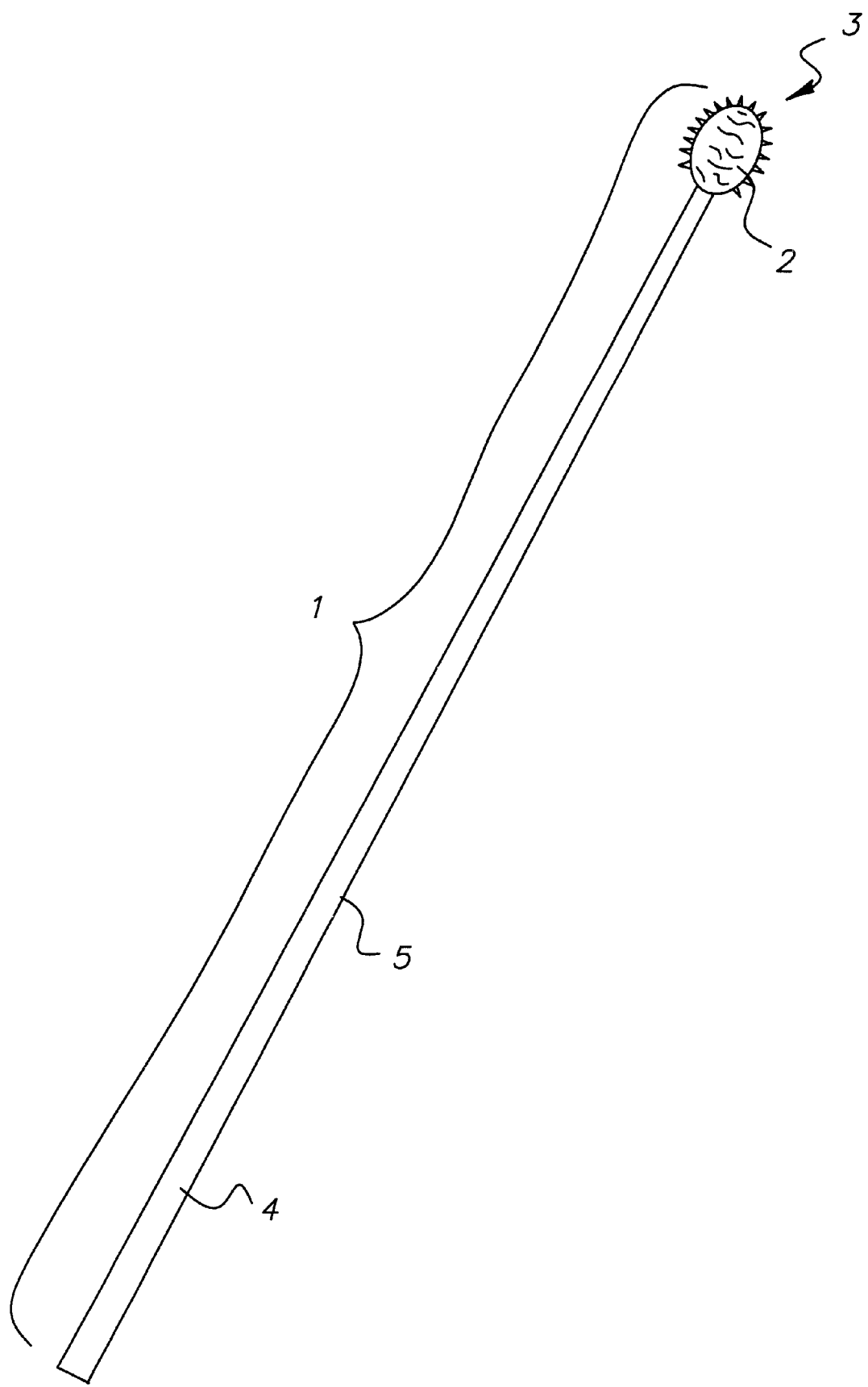

TOPICAL ANESTHETIC APPLICATOR AND METHOD OF USE

RELATED APPLICATIONS

This application claims benefit of U.S. Provisional Application Serial No. 60/166,879 filed Nov. 22, 1999, fully incorporated herein by reference.

BACKGROUND OF THE INVENTION

The present invention relates to a novel applicator for topical anesthetics and a method using said novel applicator which provides for pain-free injections in mucosa by the application of a topical anesthetic followed by an injection limited to penetrate the mucosa only to the extent of penetration of the topical anesthetic.

It is estimated that 50% of dental patients avoid treatment because of the expected pain, especially pain produced by needles and injections. In addition, stress, in the form of pain, reduces a patient's immunological response. As a result, post-operative recovery times can be extended and the risk of complications increased.

Topical anesthetics are well known in dental applications and are used to anesthetize oral tissues prior to performing certain dental procedures, such as scaling, root planing, polishing, probing, needle injection for nerve blockages, restorative bonding, suture removal, gingival curettage, tissue grafting, application of antibiotic fibers into periodontal pockets, and soft tissue biopsies.

The typical technique for application of the topical anesthetic during dental or oral surgeries involves the use of anesthetic supplied in gel or liquid form. The dentist dips an absorbent swab, made of cotton, foam, polymer or gel matrix, or the like, into the anesthetic and then transfers the anesthetic to the desired location in the patient's mouth. After the topical has anesthetized the area, a hypodermic syringe is used for delivery of further medications.

There are several drawbacks to the conventional method. First, the depth of penetration of the hypodermic exceeds the limited area of penetration of the topical anesthetic which is in the range of 2–4 mm. As a result, although the topical anesthetic reduces the amount of pain experienced prior to the hypodermic injection, the procedure is still painful due to the deeper, unlimited penetration of the hypodermic syringe. In addition, topical anesthetics are less effective when applied by swab to certain oral mucosa which are keratinized, such as the palate, due to reduced penetration through the keratin layer as compared to other mucosal surfaces. Deeper penetrations of topical anesthetic into keratinized mucosa may also take as long as 2 to 4 hours.

Unlike these other systems, the present invention provides a method that controls the depth of penetration of the hypodermic syringe. The syringe is limited in depth of penetration to the depth of mucosa anesthetized by the application of the topical anesthetic. As a result, the patient experiences greatly reduced pain. This in turn leads to shortened recovery time, reduced complications and increases the likelihood that patients in need of treatment will actually seek treatment. The method also employs a novel applicator designed to increase the penetration of the topical anesthetic into keratinized mucosa.

SUMMARY OF THE INVENTION

The present invention is a method and means for accomplishing pain-free injection in mucosa, specifically in dental applications. The method is accomplished by applying a topical anesthetic to the desired mucosal area by means of a novel applicator swab, comprising a handle on which is attached an absorbent material and an abrasive portion. The swab is dipped in topical anesthetic and placed at the desired oral location, where the abrasive portion is used to mildly abrade the oral mucosa. Immediate contact with the topical anesthetic to the slightly abraded area greatly increases the degree of penetration of the topical anesthetic into the oral tissues. The application of the topical is then followed with an injection which penetrates the tissues only to the extent of penetration of the topical anesthetic. Various devices of fixed length may be used which limit the penetration of the injection such as a drastically truncated syringe needle, a sheath fitted to and covering the needle, a needle shield, and a speculum.

DESCRIPTION OF THE DRAWINGS

FIG. 1 is a perspective view of an embodiment of the novel applicator swab.

DESCRIPTION OF THE PREFERRED EMBODIMENT

The preferred method of pain-free injection involves the use of a novel topical applicator 1 as illustrated by FIG. 1, comprising a grippable member 5, to one end of which is affixed an absorbent means 2 for holding a topical anesthetic and an abrasive means 3 for enhancing the depth of penetration of the topical anesthetic when applied to dental mucosa, and the other end of which comprises a handle 4. Further medications are then delivered into the area of mucosa anesthetized by the topical by means of a device controlling the depth of penetration of a hypodermic syringe.

The grippable member may be made of any material such as wood, metal, or plastic which can be gripped by hand and to which the absorbent and abrasive means may be affixed. An alternative embodiment may eliminate the grippable member entirely, comprising simply an absorbent material in combination with an abrasive means which is directly hand held.

The abrasive means may be any material, such as sand paper or other grit-type abrasive, bristles, rough cloth, or the like which can be affixed to the grippable member and which is capable of abrading keratinized mucosal tissue.

The absorbent means may be any absorbent material capable of being affixed to the grippable member and capable of absorbing a quantity of topical anesthetic. Such materials include, but are not limited to spun cotton or non-woven fibers, foam, or polymer or gel matrix. The absorbent material may also be pre-treated and packaged with the topical anesthetic.

To perform the method, the physician first dips the absorbent means of the applicator into topical anesthetic. The physician then lightly abrades the desired oral site with the abrasive means, followed immediately by applying the absorbent means containing the topical anesthetic to the abraded mucosal area. The application of the topical anesthetic is followed by an injection given by an injection device in which the depth of the injection is automatically limited to penetrate only into the area anesthetized by the topical. As a result, the patient experiences greatly reduced discomfort and pain.

The dipping step may be eliminated, if the absorbent material comes pre-treated with the topical.

While I have illustrated and described several embodiments of my invention herein, it will be understood that these are by way of illustration only and that various changes and modifications may be contemplated in my invention and within the scope of the following claims.

What is claimed is:

1. A novel applicator comprising:

an absorbent material; and an abrasive material combined with or attached to said absorbent material, wherein said abrasive material is capable of abrading mucosal tissue, wherein said abrasive material is a grit abrasive or rough cloth.

2. A novel applicator comprising:

a grippable member; an absorbent material affixed to said grippable member; and an abrasive material also affixed to said grippable member, wherein said abrasive material is capable of abrading mucosal tissue, wherein said absorbent material is spun cotton fibers or non-woven fibers, and wherein said abrasive material is a grit abrasive or rough cloth.

3. A novel applicator comprising:

a grippable member having proximal and distal ends, said proximal end of which comprises a handle; an absorbent material affixed to said distal end; an abrasive material also affixed to said distal end; and wherein said abrasive material is capable of abrading mucosal tissue, wherein said absorbent material is spun cotton fibers or non-woven fibers, and wherein said abrasive material is a grit abrasive or rough cloth.

4. A method for enhancing the depth of penetration of a topical anesthetic into keratinized tissue comprising:

providing a novel applicator comprising an absorbent material and an abrasive material;

abrading an area of mucosal tissue with said novel applicator;

applying a topical anesthetic to said absorbent material; and applying said topical anesthetic to said area of mucosal tissues.

5. The method of claim 4 wherein the novel applicator is pre-treated with topical anesthetic.

6. A method for pain-free injections in mucosal tissues comprising:

providing a novel applicator comprising an absorbent material and an abrasive material;

abrading an area of mucosal tissue;

applying topical anesthetic to an area of mucosal tissues;

allowing penetration into said area by said topical anesthetic; and injecting medications into said area no deeper than said penetration by said topical anesthetic.

7. A method for pain-free injections in mucosal tissues comprising:

abrading an area of mucosal tissue;

applying a topical anesthetic to said area;

allowing penetration into said area by said topical anesthetic; and injecting medications into said area no deeper than said penetration by said topical anesthetic.

* * * * *